(12) United States Patent
Wang et al.

(10) Patent No.: US 11,610,306 B2
(45) Date of Patent: Mar. 21, 2023

(54) MEDICAL IMAGE ANALYSIS METHOD AND DEVICE

(71) Applicant: INDUSTRIAL TECHNOLOGY RESEARCH INSTITUTE, Hsinchu (TW)

(72) Inventors: Ting-Yuan Wang, Taipei (TW); Ming-Shan Deng, Taichung (TW); Ya-Wen Lee, New Taipei (TW); Jung-Tzu Liu, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 155 days.

(21) Appl. No.: 17/123,967

(22) Filed: Dec. 16, 2020

(65) Prior Publication Data

US 2022/0189009 A1 Jun. 16, 2022

(51) Int. Cl.
*G06T 7/00* (2017.01)
*G06K 9/62* (2022.01)
(Continued)

(52) U.S. Cl.
CPC .............. *G06T 7/0012* (2013.01); *A61B 3/12* (2013.01); *A61B 5/4887* (2013.01);
(Continued)

(58) Field of Classification Search
CPC . G06T 2207/20081; G06T 2207/30041; G06T 2207/20084; G06T 7/0012;
(Continued)

(56) References Cited

U.S. PATENT DOCUMENTS 10,198,815 B2   2/2019  Jain et al.
10,430,946 B1 * 10/2019  Zhou .................. A61B 5/02007
(Continued)

FOREIGN PATENT DOCUMENTS

CN   104834940 A   8/2015
CN   107730507 A   2/2018
(Continued)

OTHER PUBLICATIONS

Almubarak "Two-Stage Mask-RCNN Approach for Detecting and Segmenting the Optic Nerve Head, Optic Disc, and Optic Cup in Fundus Images," May 31, 2020, MDPI (Year: 2020).*
(Continued)

*Primary Examiner* — Alex Kok S Liew
(74) *Attorney, Agent, or Firm* — Birch, Stewart, Kolasch & Birch, LLP

(57) ABSTRACT

A medical image analysis method includes: reading an original medical image; performing image classification and object detection on the original medical image to generate a first classification result and a plurality of object detection results by a plurality of complementary artificial intelligence (AI) models; performing object feature integration and transformation on a first detection result and a second detection result among the object detection results to generate a transformation result by a features integration and transformation module; and performing machine learning on the first classification result and the transformation result to generate an image interpretation result by a machine learning module and display the image interpretation result.

26 Claims, 10 Drawing Sheets lesion result matrix

[[Lesion, X, Y, W, H, C], ...]

[[1, 185, 818, 43, 42, 0.82],
 [1, 406, 964, 31, 29, 0.43],
 [1, 364, 194, 27, 27, 0.37],
 ...]

anatomic landmark result matrix

[[Structure, X, Y, W, H, C], ...]

[[1, 1016, 599, 171, 197, 0.96],
 [3, 451, 625, 220, 220, 0.33],
 ... ]

|   |   | lesion | | | | |
|---|---|---|---|---|---|---|
|   |   | $L_1$:HE | $L_2$:H | $L_3$:SE | $L_4$:NE | $L_5$:MA |
| quadrant | $S_1$ | $f(S_1,L_1)$ | $f(S_1,L_2)$ | $f(S_1,L_3)$ | $f(S_1,L_4)$ | $f(S_1,L_5)$ |
| | $S_2$ | $f(S_2,L_1)$ | $f(S_2,L_2)$ | $f(S_2,L_3)$ | $f(S_2,L_4)$ | $f(S_2,L_5)$ |
| anatomic landmark | $S_3$ | $f(S_3,L_1)$ | $f(S_3,L_2)$ | $f(S_3,L_3)$ | $f(S_3,L_4)$ | $f(S_3,L_5)$ |
| | $S_4$ | $f(S_4,L_1)$ | $f(S_4,L_2)$ | $f(S_4,L_3)$ | $f(S_4,L_4)$ | $f(S_4,L_5)$ |
| disc | $S_5$ | $f(S_5,L_1)$ | $f(S_5,L_2)$ | $f(S_5,L_3)$ | $f(S_5,L_4)$ | $f(S_5,L_5)$ |
| macula | $S_6$ | $f(S_6,L_1)$ | $f(S_6,L_2)$ | $f(S_6,L_3)$ | $f(S_6,L_4)$ | $f(S_6,L_5)$ |

(51) Int. Cl.
*G06T 3/40* (2006.01)
*G06T 7/73* (2017.01)
*G06T 7/60* (2017.01)
*A61B 5/00* (2006.01)
*A61B 3/12* (2006.01)
*G06N 20/00* (2019.01)
*G16H 30/40* (2018.01)
*G06V 10/22* (2022.01)

(52) U.S. Cl.
CPC ............ *A61B 5/7267* (2013.01); *G06K 9/629* (2013.01); *G06K 9/6256* (2013.01); *G06K 9/6267* (2013.01); *G06N 20/00* (2019.01); *G06T 3/40* (2013.01); *G06T 7/60* (2013.01); *G06T 7/73* (2017.01); *G06V 10/22* (2022.01); *G16H 30/40* (2018.01); *G06T 2207/20081* (2013.01); *G06T 2207/30041* (2013.01); *G06T 2207/30096* (2013.01); *G06T 2207/30242* (2013.01); *G06V 2201/03* (2022.01)

(58) Field of Classification Search
CPC . G06T 2207/30096; G06T 2207/10016; G06T 2207/30168; G06T 2207/10081; G06T 2207/10088; G06T 2207/30056; G06T 2207/30064; G06T 2207/30201; G06T 2207/30241; G06V 10/764; G06V 10/82; G06V 2201/03; G06V 40/167; G06V 40/168; G06V 40/174; G06V 40/20; G06N 3/0454; G06N 3/084; G06N 20/00; G06N 3/0445; G06N 3/0481; G06N 3/08; G06N 10/00; G06N 3/02
See application file for complete search history.

(56) References Cited

U.S. PATENT DOCUMENTS

| 10,572,996 B2 | 2/2020 | Eurén |
| 2019/0050982 A1 | 2/2019 | Song et al. |
| 2019/0286990 A1 | 9/2019 | Kenney et al. |
| 2020/0085382 A1 | 3/2020 | Taerum et al. |
| 2020/0160510 A1 | 5/2020 | Lindemer et al. |
| 2020/0211180 A1 | 7/2020 | Gillies et al. |

FOREIGN PATENT DOCUMENTS

| CN | 108280827 A | 7/2018 |
| CN | 108376558 A | 8/2018 |
| CN | 109685809 A | 4/2019 |
| CN | 109978882 A | 7/2019 |
| CN | 110197492 A | 9/2019 |
| CN | 110458249 A | 11/2019 |
| CN | 110458883 A | 11/2019 |
| CN | 110516759 A | 11/2019 |
| CN | 110931112 A | 3/2020 |
| TW | M469047 U | 1/2014 |
| TW | 201926359 A | 7/2019 |
| TW | 202036592 A | 10/2020 |
| TW | 202040585 A | 11/2020 |
| WO | WO 2018/069736 A1 | 4/2018 |
| WO | WO 2018/189541 A1 | 10/2018 |
| WO | WO 2018/189551 A1 | 10/2018 |
| WO | WO 2018/222755 A1 | 12/2018 |
| WO | WO 2018/227105 A1 | 12/2018 |
| WO | WO 2019/005722 A1 | 1/2019 |
| WO | WO 2019/103912 A2 | 5/2019 |
| WO | WO 2019/222135 A1 | 11/2019 |
| WO | WO 2020/020809 A1 | 1/2020 |

OTHER PUBLICATIONS

Taiwanese Office Action and Search Report for Taiwanese Application No. 109144443, dated Oct. 5, 2021.
Taiwanese Office Action and Search Report for Taiwanese Application No. 110137780, dated Aug. 12, 2022.

* cited by examiner

|  | $L_1$:HE | $L_2$:H | $L_3$:SE | $L_4$:NE | $L_5$:MA |
|---|---|---|---|---|---|
| $S_1$ | $f(S_1,L_1)$ | $f(S_1,L_2)$ | $f(S_1,L_3)$ | $f(S_1,L_4)$ | $f(S_1,L_5)$ |
| $S_2$ | $f(S_2,L_1)$ | $f(S_2,L_2)$ | $f(S_2,L_3)$ | $f(S_2,L_4)$ | $f(S_2,L_5)$ |
| $S_3$ | $f(S_3,L_1)$ | $f(S_3,L_2)$ | $f(S_3,L_3)$ | $f(S_3,L_4)$ | $f(S_3,L_5)$ |
| $S_4$ | $f(S_4,L_1)$ | $f(S_4,L_2)$ | $f(S_4,L_3)$ | $f(S_4,L_4)$ | $f(S_4,L_5)$ |
| $S_5$ | $f(S_5,L_1)$ | $f(S_5,L_2)$ | $f(S_5,L_3)$ | $f(S_5,L_4)$ | $f(S_5,L_5)$ |
| $S_6$ | $f(S_6,L_1)$ | $f(S_6,L_2)$ | $f(S_6,L_3)$ | $f(S_6,L_4)$ | $f(S_6,L_5)$ |

$S_1$–$S_4$: quadrant; $S_5$: disc; $S_6$: macula (anatomic landmark); $L_1$–$L_5$: lesion

FIG. 7 lesion result matrix

[[Lesion, X, Y, W, H, C], ...]

[[1, 185, 818, 43, 42, 0.82],
[1, 406, 964, 31, 29, 0.43],
[1, 364, 194, 27, 27, 0.37],
...]

anatomic landmark result matrix

[[Structure, X, Y, W, H, C], ...]

[[1, 1016, 599, 171, 197, 0.96],
[3, 451, 625, 220, 220, 0.33],
...]

MEDICAL IMAGE ANALYSIS METHOD AND DEVICE

TECHNICAL FIELD

The disclosure relates in general to a medical image analysis method and device.

BACKGROUND

To increase doctors' efficiency in the interpretation of medical images and reduce human errors, it has become a prominent task in the development of artificial intelligence (AI) medicine to assist the interpretation of medical images using AI technology.

The AI-based image auxiliary diagnosis for medical image mainly involves three tasks, namely object detection, segmentation and classification. For example, the classification task can determine whether a tumor is benign or malignant, and the simple classification of disease severity enables medical resources to be more effectively allocated. Normally, the classification of lesion severity based on medical images is performed by classifiers such as deep neural networks (DNN), support vector machine (SVM, one type of machine learning), and random forest.

Due to the fact that the classification task for a specific disease is closely related to lesions and anatomic landmarks, even an experienced doctor may find it difficult providing clear-cut rules for deciding how and degree they are related to each other, and it is nontrivial to find an analytical solution for the relevance. However, the AI technology is ideal for resolving such type of problems through the learning of labeled data. The past experience shows that when only one single AI classification model or one AI single lesion object detection model is used, the accuracy rate cannot be satisfactory. If the object detection model can be assisted by the classification model and vice versa, the disadvantage of using one single model can be resolved, and the misinterpretation rate can be reduced.

Moreover, the training data may have a small data volume and the lesion may be very minor at the initial stage of the disease development. Under such circumstance, if the classification task of medical images entirely relies on a single classifier, when the features area used to differentiate normal images from abnormal images is relatively small in area, the lesions may not be effectively recognized, and the result of disease classification will be incorrect.

SUMMARY

According to one embodiment, a medical image analysis method is provided. The medical image analysis method includes: reading an original medical image; performing image classification and object detection on the original medical image to generate a first classification result and a plurality of object detection results by a plurality of complementary artificial intelligence (AI) models; performing object feature integration and transformation on a first detection result and a second detection result among the object detection results to generate a transformation result by a features integration and transformation module; and performing machine learning on the first classification result and the transformation result to generate an image interpretation result by a machine learning module and display the image interpretation result.

According to another embodiment, a medical image analysis device is provided. The medical image analysis device includes a processor; and a display unit coupled to the processor, wherein, the processor is configured to: read an original medical image; perform image classification and object detection on the original medical image to generate a first classification result and a plurality of object detection results by a plurality of complementary artificial intelligence (AI) models; perform object feature integration and transformation on a first detection result and a second detection result among the object detection results to generate a transformation result by a features integration and transformation module; and perform machine learning on the first classification result and the transformation result to generate an image interpretation result by a machine learning module and display the image interpretation result on the display unit.

The above and other aspects of the invention will become better understood with regard to the following detailed description of the preferred but non-limiting embodiment(s). The following description is made with reference to the accompanying drawings.

BRIEF DESCRIPTION OF THE DRAWINGS

FIG. 7 is a lesion and anatomic landmark relation matrix according to an embodiment of the present disclosure.

DETAILED DESCRIPTION

Technical terms are used in the specification with reference to generally-known terminologies used in the technology field. For any terms described or defined in the specification, the descriptions and definitions in the specification shall prevail. Each embodiment of the present disclosure has one or more technical features. Given that each embodiment is implementable, a person ordinarily skilled in the art can selectively implement or combine some or all of the technical features of any embodiment of the present disclosure.

Currently, referable diabetic macular edema (DME) is defined as any hard exudates (HE) occurring within a distance from the macula center, wherein the distance is the disc diameter. Conversely, no occurrence of hard exudates within a disc diameter of distance from the center of macula is regarded as non-referable macular edema.

Other than DME, the respectability assessment of pancreatic cancer tumor using the computed tomography (CT) before the surgery is performed can be divided into 5 grades, from grade 0 to grade 4. The grade is relevant to the degree of the tumor contacting the vessel. The larger the degree of the tumor contacting the vessel, the larger the grade.

Figure 1:
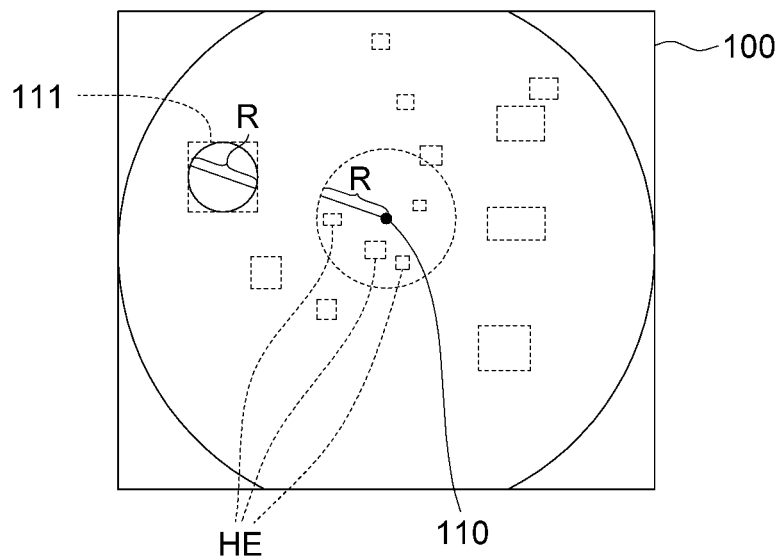
FIG. 1 is a schematic diagram of diabetic macular edema.

Refer to FIG. 1. In the original medical image 100, a virtual circle is simulated using the macula center 110 as the circle center and the diameter R of the disc 111 as the radius of the circle. When a hard exudate HE is found within the virtual circle, this situation can be regarded as referable DME.

Figure 2:
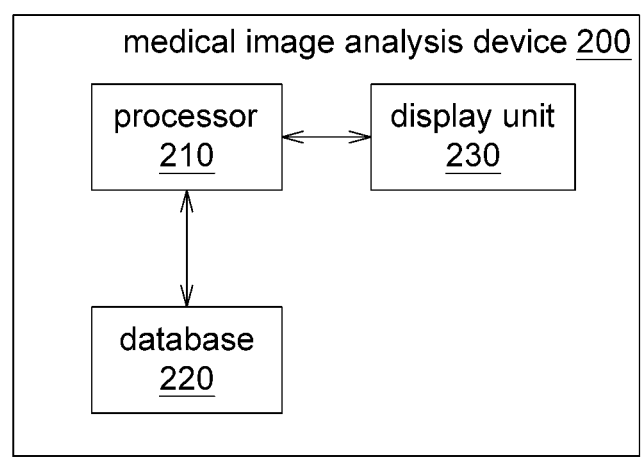
FIG. 2 is a functional diagram of a medical image analysis device according to an embodiment of the present disclosure.

FIG. 2 is a functional diagram of a medical image analysis device 200 according to an embodiment of the present disclosure. The medical image analysis device 200 includes a processor 210, a database 220 and a display unit 230. The processor 210 is coupled to the database 220 and the display unit 230. The processor 210 reads an original medical image from the database 220. Then, the processor 210 further analyzes and interprets the original medical image to generate an image interpretation result and display the image interpretation result on the display unit 230. The processor 210 can be realized by a central processing unit (CPU), or other programmable general-purpose micro control unit (MCU), such as microprocessor, digital signal processor (DSP), programmable processor, application specific integrated circuit (ASIC), graphics processing unit (GPU), arithmetic logic unit (ALU), complex programmable logic device (CPLD), field programmable gate array (FPGA) or other similar elements or a combination thereof. The display unit 230 can be realized by a device with display function, such as but not limited to a liquid crystal display (LCD).

Figure 3:
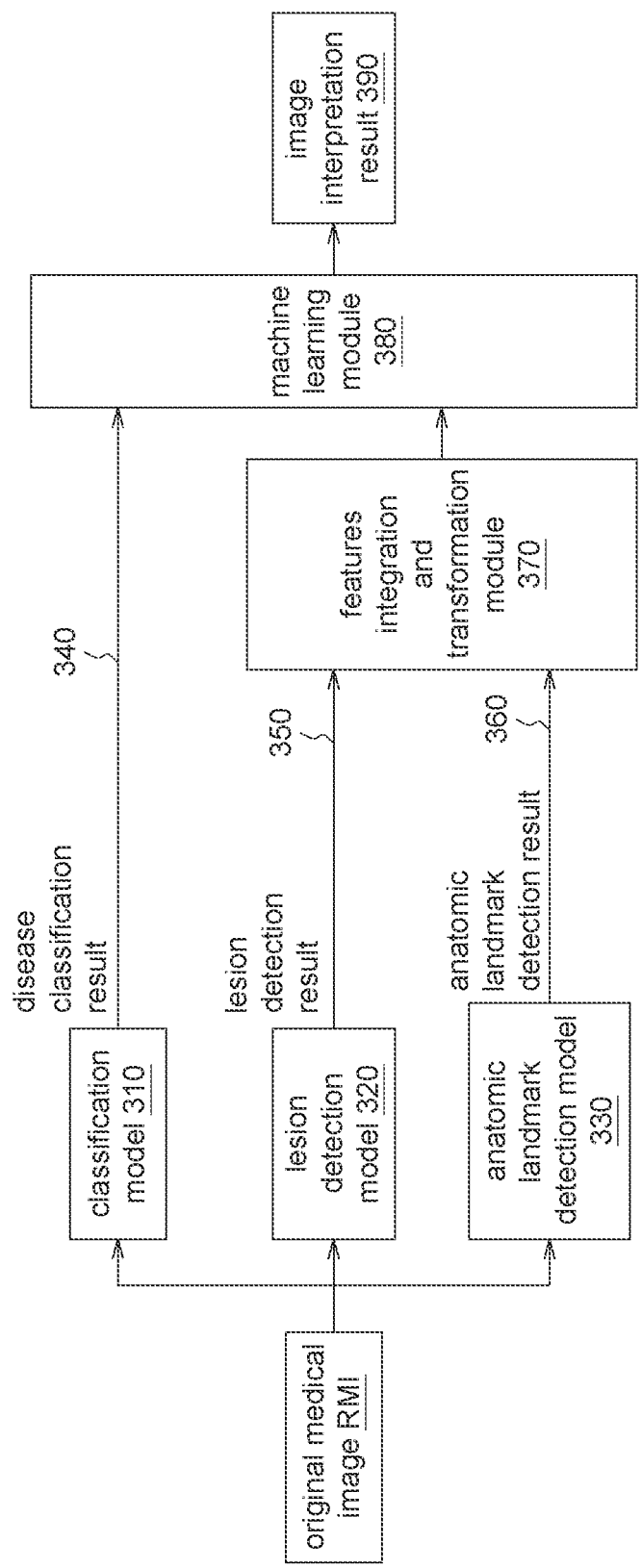
FIG. 3 is a schematic diagram of medical image analysis according to an embodiment of the present disclosure.

FIG. 3 is a schematic diagram of medical image analysis according to an embodiment of the present disclosure. As shown in FIG. 3, the original medical image RMI is respectively inputted to plural artificial intelligence (AI) models, each performing a different task, such as but not limited to a classification model 310, a lesion detection model 320 and an anatomic landmark detection model 330, each performing a different task.

The classification model 310 is a disease classification model and is used to analyze the entire original medical image RMI to generate a disease classification result 340.

The lesion detection model 320 is a lesion detection model pertaining to a specific disease and is used to analyze the original medical image RMI to generate a lesion detection result 350. The lesion detection result 350 includes information of the position, the area and the confidence of each lesion, and the total number of lesions for each lesion category. Selectively, the area of each lesion may be calculated using the vertical length and the horizontal length of the bounding box detected by the lesion detection model 320. Here, the lesion is such as but not limited to hard exudates.

The anatomic landmark detection model 330 is an anatomic landmark (including organs, tissues) detection model for a specific disease and is used to analyze the original medical image RMI to generate an anatomic landmark detection result 360. The anatomic landmark detection result 360 includes information of the position, the vertical length (a first length), the horizontal length (a second length) and the confidence of each anatomic landmark. Selectively, the area of each anatomic landmark may be calculated using the vertical length and the horizontal length of the bounding box detected by the anatomic landmark detection model 330. Here, the anatomic landmark is such as but not limited to disc and macula.

The lesion detection result 350 and the anatomic landmark detection result 360 are inputted to the features integration and transformation module 370 for performing integration and transformation on object features (such as but not limited to lesion and anatomic landmarks). More specifically, the features integration and transformation module 370 can transform the lesion detection result and the anatomic landmark detection result to obtain a scalar or a vector. The transformation result (scalar or vector) of the features integration and transformation module 370 along with the disease classification result 340 are inputted to a machine learning module 380. Through a machine learning (ML) algorithm, the machine learning module 380 can learn several prediction rules for generating an image interpretation result 390, which includes information of the probability of DME and can be inputted to the display unit 230.

The object detection result (scalar or vector) and the disease classification result 340 can be regarded as plural items of training data for training the machine learning module 380 to generate an image interpretation result, each item of training data includes an object detection result (scalar or vector) and a disease classification result 340.

In one embodiment of the present disclosure, the features integration and transformation module 370 and the machine learning module 380 can be realized with a chip, a circuit block in the chip, a firmware circuit, a circuit board containing several electronic components and wires or a storage medium that stores plural application programming codes, or realized by an electronic device, such as a computer system or a server, performing corresponding software or programs. The features integration and transformation module 370 and the machine learning module 380 are executed by the processor 210 of FIG. 2.

Figure 4:
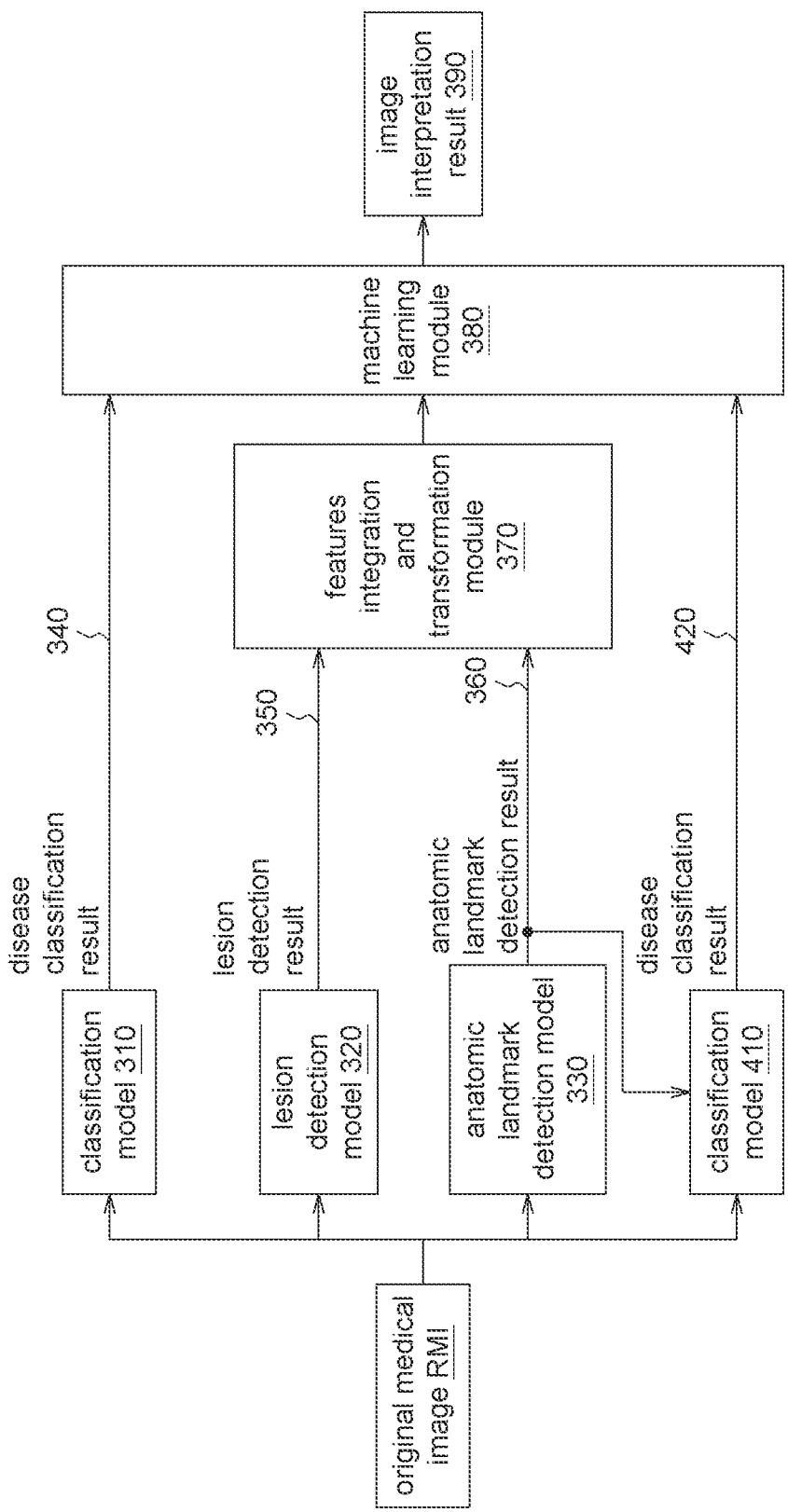
FIG. 4 is a schematic diagram of medical image analysis according to another embodiment of the present disclosure.

FIG. 4 is a schematic diagram of medical image analysis according to another embodiment of the present disclosure. As shown in FIG. 4, the original medical image RMI is inputted to plural artificial intelligence (AI) models performing multiple tasks, such as but not limited to the classification model 310, the lesion detection model 320, the anatomic landmark detection model 330 and the classification model 410.

As shown in FIG. 4, the anatomic landmark detection result 360 (e.g. a target region) generated by the anatomic landmark detection model 330 is inputted to classification model 410. For example, the classification model 410 takes the macula region of the original medical image RMI as input. Selectively, the macula region can be defined by a bounding box of the anatomic landmark detection result 360 for can be defined by using the macula center and the disc diameter, wherein the macular center and the disc diameter are calculated using the anatomic landmark detection result 360, and analyzed by the classification model 410 to generate a disease classification result 420. One key aspect of one embodiment of the present invention is that the macula region is defined by the anatomic landmark detection model 330, and is used as input to the classification model 410. More specifically, during the training/prediction process of the classification model 410, it is the defined macula region that will be used as the input image, rather than the entire original medical image RMI. Compared to using the entire original medical image RMI as input to the classification model 410, such defined region is much less likely to become undetectable by the classification model 410 even after subjecting to the image reduction operation that is often employed for saving computation time during the deep learning/prediction process. This desirable effect is especially useful when the lesion or landmark is very small or tiny relative to the entire original medical RMI image. It guarantees the capability of the classification model 410 in learning identification of small objects in macula region.

As shown in FIG. 4, the disease classification result 420 of the classification model 410 is also inputted to the machine learning module 380.

The operation principles of the features integration and transformation module 370 are disclosed below.

Figure 5A:
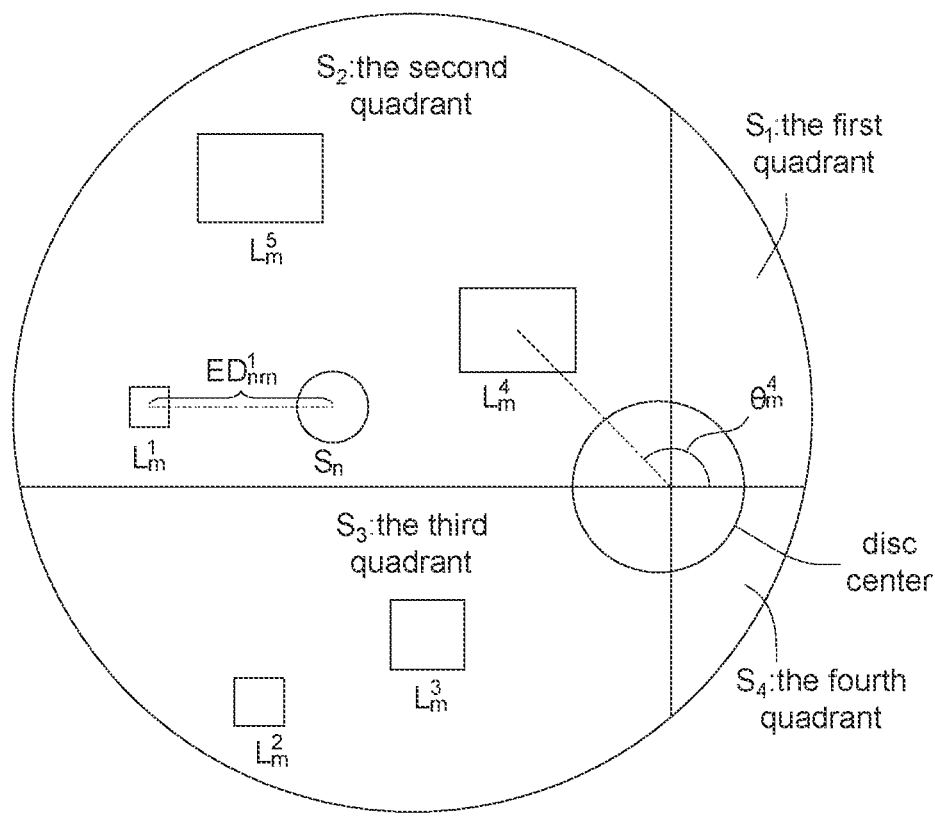
FIG. 5A is a schematic diagram of dividing the fundus image into four quadrants using the disc center as the center point according to an embodiment of the present disclosure.

FIG. 5A is a schematic diagram of dividing the fundus image into 4 quadrants using the disc as the central point according to an embodiment of the present disclosure. In FIG. 5A, symbols $S_1 \sim S_4$ respectively represent the first quadrant to the fourth quadrant, and $S_n$ represents the n-th anatomic landmark, such as macula and quadrant (n is a positive integer). In one embodiment of the present disclosure, n=1~6, and the range of n can be adjusted according to actual needs. That is, in the embodiments of the present disclosure, the quadrant itself also represents an anatomic landmark. $L_m^i$ represents an i-th lesion of the m-th lesion category. For example, $L_1^1$ represents a first hard exudate, $L_1^3$ represents a third hard exudate. $ED_{nm}^i$ represents a relative distance between the lesion $L_m^i$ and the anatomic landmark $S_n$, wherein $0 \leq ED_{nm}^i \leq 1$. For example, $ED_{nm}^1$ represents a relative distance between the lesion $L_m^1$ and the anatomic landmark $S_n$.

In one embodiment of the present disclosure, take the relation between the quadrants (n=1~4) and the lesions as an illustrative example. The features integration and transformation module 370 considers any combination of the following parameters: the relationship between an individual lesion and the respective quadrant, the area of each lesion, and the confidence (level) of the lesion. In one embodiment of the present disclosure, a transform that specifies a positive correlation of (1) the membership degree of angular, (2) the area, (3) the confidence, or any combination thereof is calculated. In one embodiment of the present disclosure, the first positive correlation between the quadrants and the lesion can be represented by such as but not limited to equation 1 below:

$$f(S_n, L_m) = \sum_{i=1}^{N} G_{S_n}(\theta_m^i)^p \times (A_m^i)^q \times (Conf_m^i)^r. \quad (1)$$

In equation (1), parameters p, q and r can be obtained through data learning. The membership degree of angular can be represented using a fuzzy function (FIG. 6), the angle $\theta_m^i$ represents an angle (radian) between the lesion $L_m^i$ and the horizontal axis, $G_{S_n}(\theta_m^i)$ represents a degree of angular membership. $A_m^i$ represents a relative area of the lesion $L_m^i$, $Conf_m^i$ represents a confidence, and $G_{S_n}(\theta_m^i)$ represents an angular membership function, wherein, $0 \leq A_m^i$, $Conf_m^i$, $G_{S_n}(\theta_m^i) \leq 1$. According to the plane coordinate system used in one embodiment of the present disclosure, the disc center is used as the origin, the horizontal line is used as the horizontal axis, and the vertical line is used as the vertical axis. That is, the first positive correlation between the quadrants and the lesion is transformed by a first operation result $(G_{S_n}(\theta_m^i)^p)$ of the membership degree of angular and a first parameter (p), a second operation result $((A_m^i)^q)$ of the area and a second parameter (q), and a third operation result $((Conf_m^i)^r)$ of the confidence and a third parameter (r).

In one embodiment of the present disclosure, let the relation between the anatomic landmark and the lesion be taken as an illustrative example. The features integration and transformation module 370 considers any combination of the relationship between the lesion and the anatomic landmark (for example, a reciprocal of a distance between the lesion and the anatomic landmark), the area of the lesion, and the confidence of the lesion. In one embodiment of the present disclosure, the transform that specifies a positive correlation of: (1) the reciprocal of the distance between the lesion and the anatomic landmark, (2) the area of the lesion, (3) the confidence of the lesion, or any combination thereof is calculated. In one embodiment of the present disclosure, the second positive correlation between the anatomic landmark and of the lesion can be represented by such as but not limited to equation (2) below:

$$f(S_n, L_m) = \sum_{i=1}^{N} \left(\frac{1}{ED_{nm}^i}\right)^p \times (A_m^i)^q \times (Conf_m^i)^r. \quad (2)$$

In equation (2), parameters q', q' and r' can be obtained through data learning. That is, the second positive correlation between an anatomic landmark and a lesion is relevant to the follows: a fourth operation result $$\left(\left(\frac{1}{ED_{nm}^i}\right)^p\right)$$

of the reciprocal of the distance between the lesion and the anatomic landmark and the fourth parameter (the parameter p'), a fifth operation result $((A_m^i)^{q'})$, of the area and the fifth parameter (the parameter q'), and a sixth operation result $((Conf_m^i)^{r'})$ of the confidence and the sixth parameter (the parameter r').

Figure 5B:
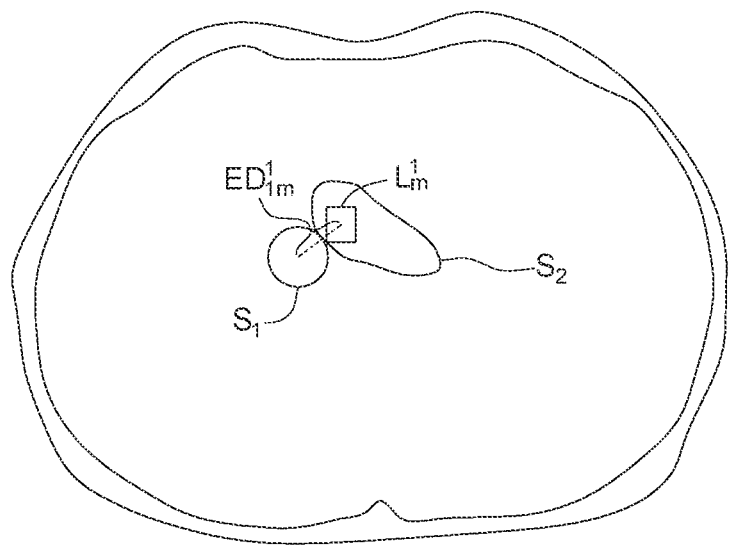
FIG. 5B is an exemplified range of a non-fundus image according to another embodiment of the present disclosure.

FIG. 5B is an exemplified range of a non-fundus image according to another embodiment of the present disclosure. In FIG. 5B, $S_1$ and $S_2$ represent 2 categories of anatomic landmarks, respectively. For example, $S_1$ and $S_2$ represent a vessel tissue and a pancreatic tissue respectively. $L_m^i$ represents an i-th lesion (such as pancreas tumor) of the m-th lesion category, and $EDh_{nm}^i$ represents a relative distance between the lesion $L_m^i$ and the anatomic landmark $S_n$, wherein $0 \leq ED_{nm}^i \leq 1$. For example, $ED_{im}^1$ represents the relative distance between the lesion $L_m^1$ and the anatomic landmark $S_1$.

Similarly, in one embodiment of the present disclosure as shown in FIG. 5B, let the relation between the anatomic landmark (such as vessel or pancreas) and the lesion (such as pancreas tumor) be taken for example. The features integration and transformation module 370 considers any combination of the relevance between the lesion and the anatomic landmark (for example, the reciprocal of the distance between the lesion and the anatomic landmark), the area, and the confidence. In one embodiment of the present disclosure, a transform specifies a positive correlation with (1) the reciprocal of the distance between the lesion and the anatomic landmark, (2) the area, (3) the confidence, or any combination thereof. The second positive correlation between the anatomic landmark and the lesion can be represented by equation (2), and the details are not repeated here.

Figure 6:
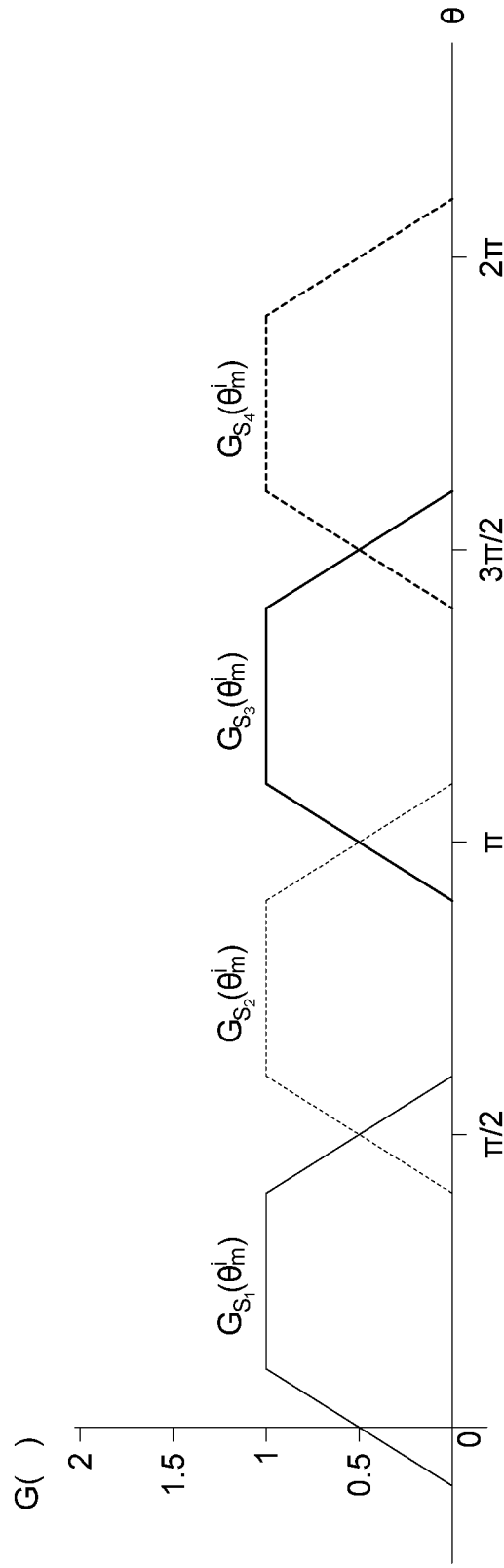
FIG. 6 is a schematic diagram of an angular membership function according to an embodiment of the present disclosure.

The said angular membership function can be obtained using the fuzzy logic. More specifically, as shown in FIG. 6, four fuzzy sets can be defined, wherein the function has an output between 0 and 1. Besides, the angular membership function can have a shape of such as but not limited to a trapezoid, a triangle or any combination thereof, and the shape can be trained (the shape can be trained).

In the embodiments of the present disclosure, when n=1~4 (quadrant), parameter $\mathrm{Conf}_m^i$ in equation (1) represents the confidence outputted by the lesion detection model 320 for the lesion. That is, when n=1~4 (quadrant), a transformed value is calculated according to equation (1) using an angular membership function, an area parameter and a confidence parameter. The larger the confidence parameter $\mathrm{Conf}_m^i$, the larger the probability of the existence of the lesion.

In one embodiment of the present disclosure, when n=5~6 (the anatomic landmark), an output value is calculated according to equation (2) using a distance parameter (particularly, the reciprocal of the distance parameter), an area parameter and a confidence parameter.

In one embodiment of the present disclosure, parameters p, q, r, p', q' and r' are real numbers and can be updated during model training. An optimal solution of the parameters p, q, r, p', q' and r' can be obtained through such as but not limited to the well-known backpropagation algorithm. Also, an optimal solution of the parameters p, q, r, p', q' and r' can be obtained through Bayesian optimization, wherein when Bayesian optimization is used, the values of p, q, r, p', q' and r' are subjected to the following restriction: 0≤p, q, r, p', q', r'. The parameters p, q, r, p', q' and r' can be updated through backpropagation or Bayesian optimization.

In one embodiment of the present disclosure, the features integration and transformation module 370 transforms the lesion detection result 350 and the anatomic landmark detection result 360 into a feature vector or a scalar, that is, function $f(S_n, L_m)$.

To put it in greater details, the lesion detection result 350 generated by the lesion detection model 320 can be a lesion result matrix as shown in FIG. 7. In the lesion result matrix, the elements in each row include: [Lesions, X, Y, W, H, C], wherein, Lesions, X, Y, W, H, C respectively represent the X coordinate (X) of the lesion position, the Y coordinate (Y) of the lesion position, the horizontal length (W) of the lesion, the vertical length (H) of the lesion, and the confidence (C) of the lesion of the lesion category (Lesion) marked by the lesion detection model.

The anatomic landmark detection result 360 generated by the anatomic landmark detection model 330 is an anatomic landmark result matrix as shown in FIG. 7. In the anatomic landmark result matrix, the elements in each row include: [Structure, X, Y, W, H, C], wherein, Structure, X, Y, W, H, C respectively represent the forecast of the X coordinate (X) of the anatomic landmark position, the Y coordinate (Y) of the anatomic landmark position, the horizontal length (W) of the anatomic landmark, the vertical length (H) of the anatomic landmark, the confidence (C) of the anatomic landmark of the anatomic landmark category (Structure) marked by the anatomic landmark detection model.

The features integration and transformation module 370 integrates the lesion result matrix and the anatomic landmark result matrix as a lesion and anatomic landmark relation matrix (FIG. 7). The relation and severity of corresponding anatomic landmark of each category and corresponding lesion of each category in the lesion and anatomic landmark relation matrix can be obtained through transformation. In FIG. 7, suppose there are 5 categories of lesions: $L_1$ represents hard exudates (HE), $L_2$ represents hemorrhage (H), $L_3$ represents soft exudates (SE), $L_4$ represents neovascularization (NE), and $L_5$ represents microaneurysm (MA).

Figure 8:
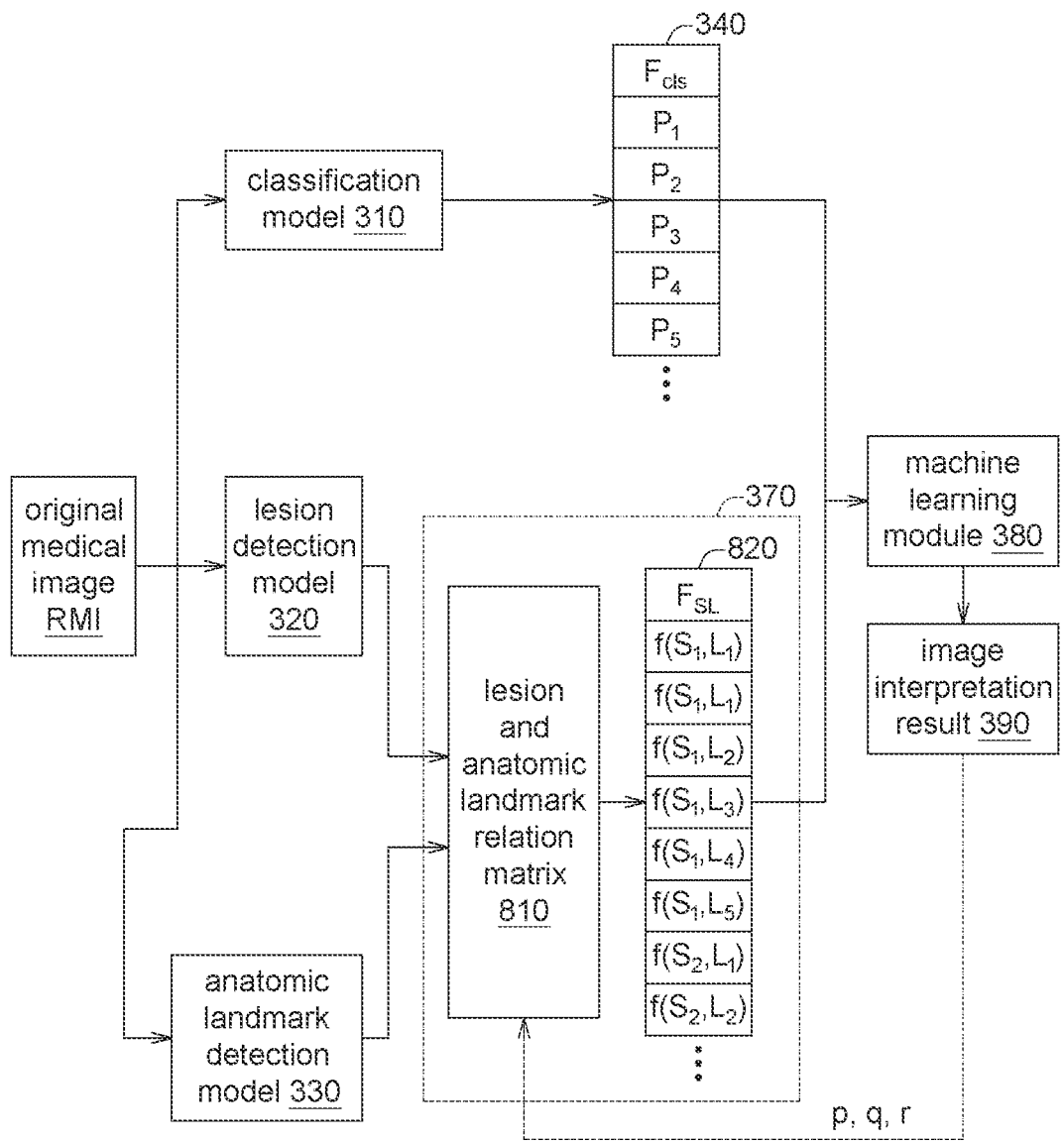
FIG. 8 is a schematic diagram of several AI model outputs being combined and inputted to a machine learning module according to an embodiment of the present disclosure.

FIG. 8 is a schematic diagram of plural AI models outputs being combined and inputted to a machine learning module 380 according to one embodiment of the present disclosure. As shown in FIG. 8, the disease classification result 340 of the classification model 310 can be represented as a one-dimensional confidence matrix. As aforesaid, the features integration and transformation module 370 integrates the lesion detection result 350 (can be represented as a lesion result matrix) and the anatomic landmark detection result 360 (can be represented as an anatomic landmark result matrix) into a lesion and anatomic landmark relation matrix. Then, the features integration and transformation module 370 flattens the lesion and anatomic landmark relation matrix 810 into a one-dimensional lesion and anatomic landmark relation vector 820. The disease classification result 340 (one-dimensional confidence matrix) and the one-dimensional lesion and anatomic landmark relation vector 820 are inputted to the machine learning module 380 to generate the image interpretation result 390 using a machine learning algorithm.

Figure 9:
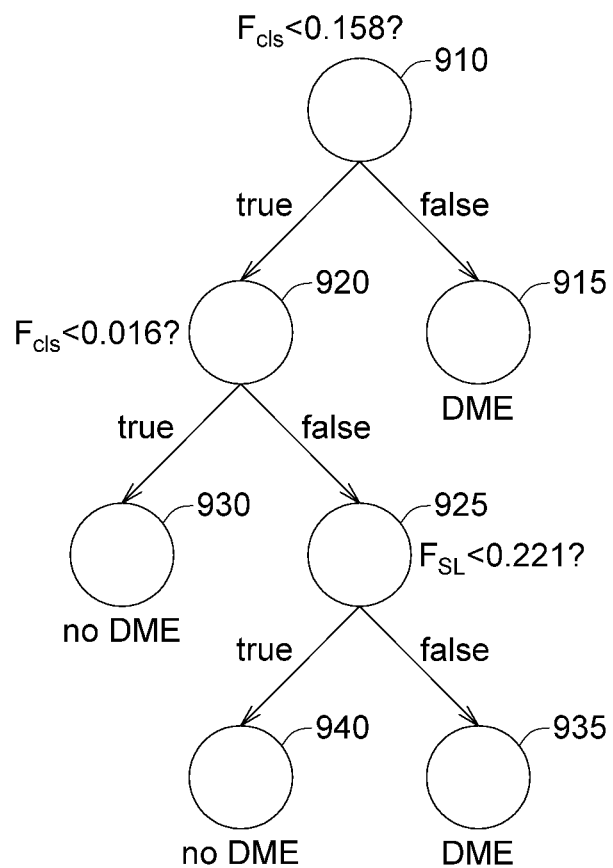
FIG. 9 is a schematic diagram of a machine learning algorithm according to an embodiment of the present disclosure.

In one embodiment of the present disclosure, aforesaid machine learning algorithm can be realized by a decision tree but is not limited thereto. FIG. 9 is an illustrative tree as a training result of a machine learning algorithm according to an embodiment of the present disclosure. As shown in FIG. 9, whether the confidence $F_{cls}$ is less than 0.158 is judged in node 910. If the decision result in node 910 is false, then proceed to node 915, and it is determined that DME exists. If the decision result in node 910 is true, then proceed to node 920 to determine whether the confidence $F_{cls}$ is less than 0.016. If the decision result in node 920 is true, then proceed to node 930, and it is determined that DME does not exist. If the decision result in node 920 is false, then proceed to node 925 to determine whether the confidence $F_{SL}$ is less than 0.221. If the decision result in node 925 is false, then proceed to node 935, and it is determined that DME exists. If the decision result in node 925 is true, then proceed to node 940, and it is determined that DME does not exist.

Figure 10:
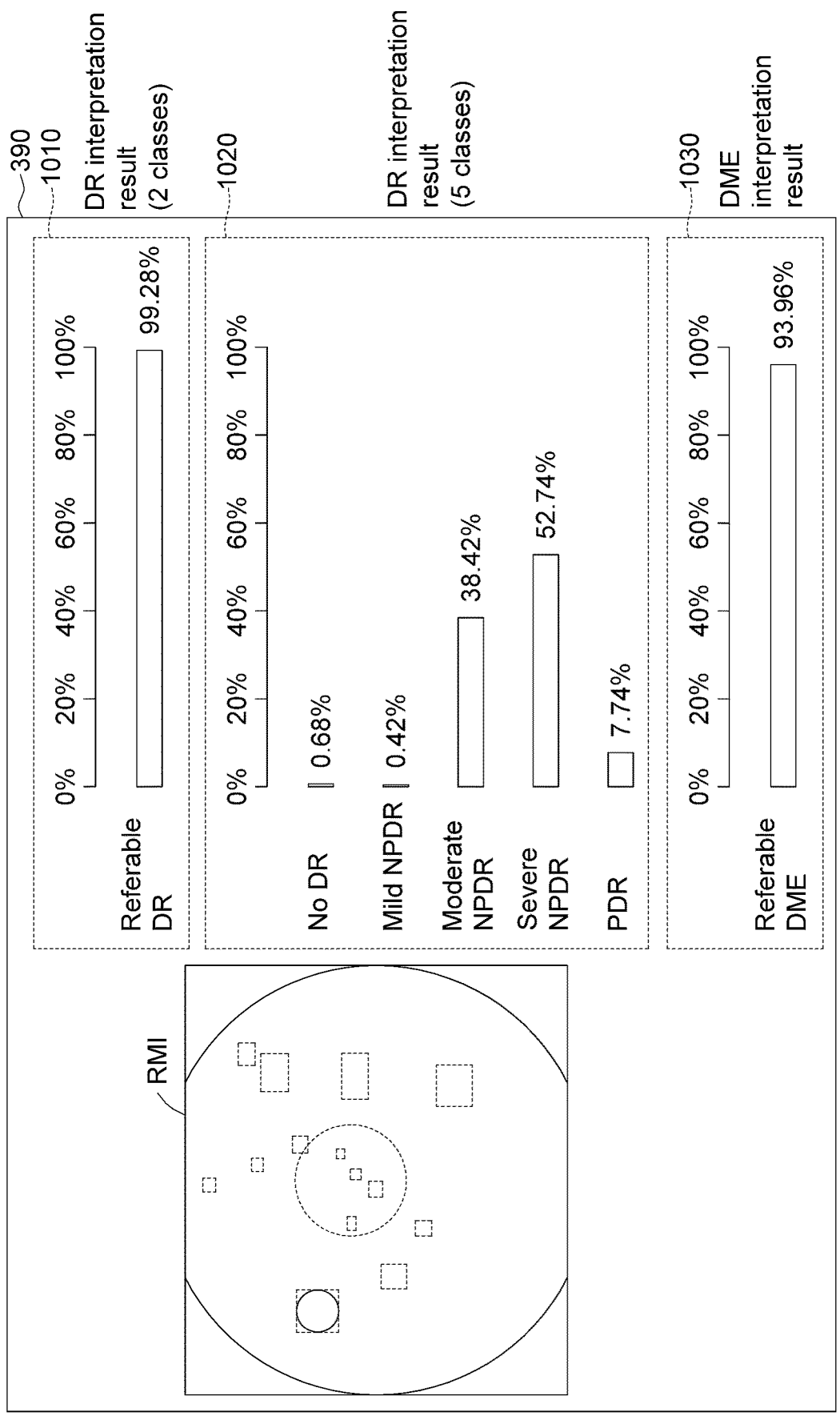
FIG. 10 is an example of an image interpretation result displayed on the display unit according to an embodiment of the present disclosure.

FIG. 10 is an example of an image interpretation result displayed on the display unit 230 according to an embodiment of the present disclosure. As shown in FIG. 10, the image interpretation result 390 includes an original medical image RMI (such as but not limited to an eye image, and the lesion and the anatomic landmark are displayed), a DR interpretation result (2 classes) 1010, a DR interpretation result (5 classes) 1020 and DME interpretation result 1030. FIG. 10 is an example of the image interpretation result 390, but the present disclosure is not limited thereto.

Figure 11:
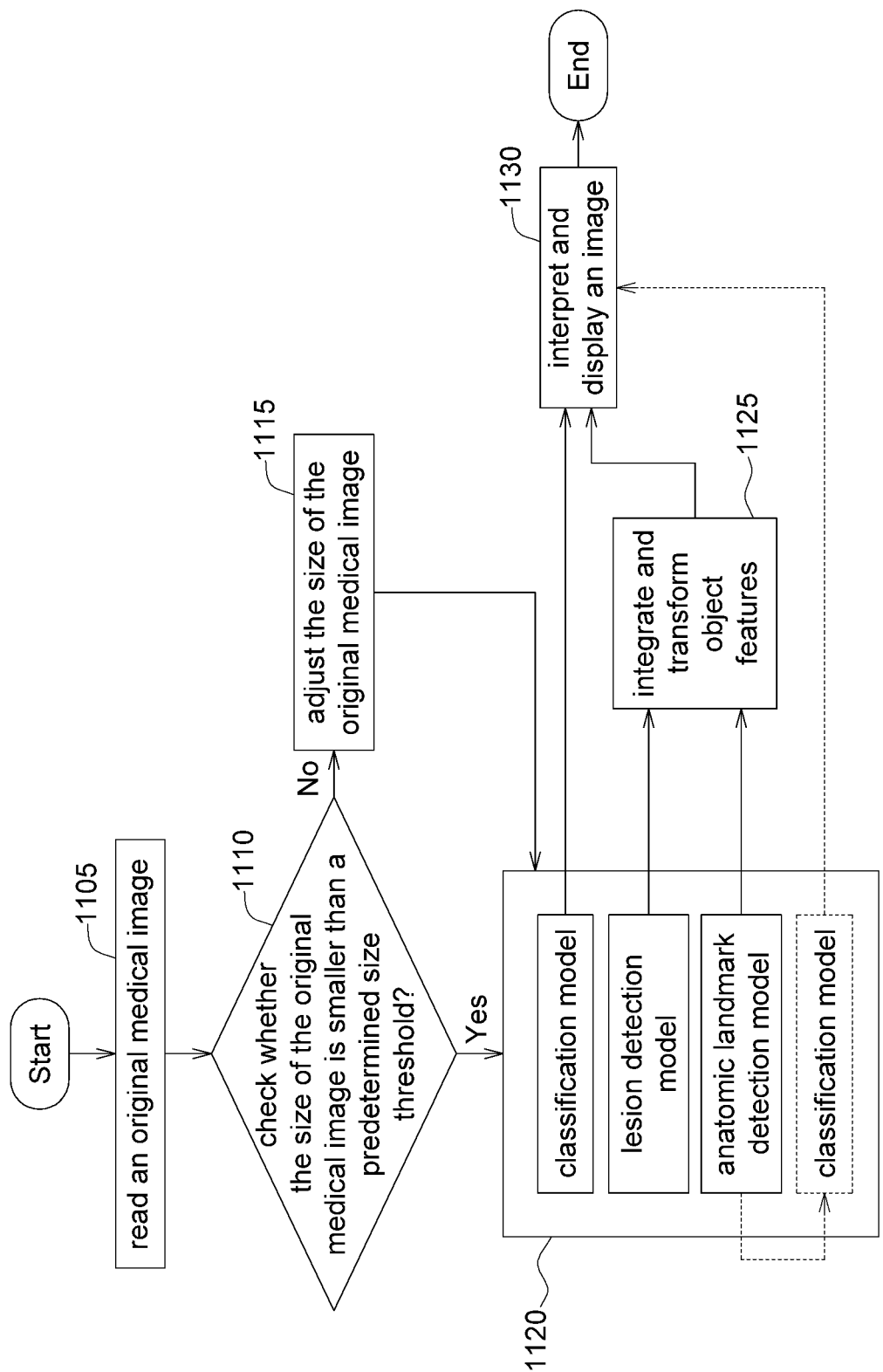
FIG. 11 is a flowchart of a medical image analysis method according to an embodiment of the present disclosure.

FIG. 11 is a flowchart of a medical image analysis method according to an embodiment of the present disclosure. As shown in FIG. 11, in step 1105, an original medical image is read. In step 1110, whether the size of the original medical image is smaller than a predetermined size threshold is checked. If the determination outcome in step 1110 is negative, then the method proceeds to step 1115, the size of the original medical image is adjusted to be smaller than predetermined size threshold. If the determination in step 1110 is true, then proceed to step 1120, image classification and object detection is performed on the medical image to generate a first classification result and plural object detection results by plural complementary AI models (such as the classification model, the lesion detection model, and the anatomic landmark detection model). In step 1125, object features (such as but not limited to the lesion and the anatomic landmark) are subjected to integration and transformation on the two detection results among the detection results to generate a transformation result. In step 1130, machine learning is performed on the transformation result and the first classification result to generate an image interpretation result and display the image interpretation result.

The original medical image can be a fundus image (FIG. 5A) or a non-fundus image (FIG. 5B) and is still within the scope of protection of the present disclosure.

Details of steps 1120, 1125 and 1130 are the same as the above disclosure and are not repeated here.

The performance difference between the prior art and the embodiments of the present disclosure are compared in terms of disease severity of DME and the comparison result is shown below:

|  | Sensitivity | Specificity | Accuracy |
|---|---|---|---|
| Using a classification model | 84.61% | 93.46% | 93.56% |
| Using a lesion detection model and an anatomic landmark detection model | 82.52% | 93.36% | 92.47% |
| The embodiments of the present disclosure | 90.91% | 94.24% | 93.97% |

It can be seen from the above table that the embodiments of the present disclosure have better performance in terms of sensitivity, specificity and accuracy.

The embodiments of the present disclosure disclose a medical image analysis method and system assisted by lesion detection and anatomic landmark detection, particularly the medical image analysis method and system integrates plural AI models each performing a different task.

According to the embodiments of the present disclosure, relevant AI models (such as the classification model, the lesion detection model, and the anatomic landmark detection model) are complementarily integrated to perform various different tasks, thereby effectively increasing the overall system performance in classifying severity of diseases, and therefore increasing the accuracy in the interpretation of medical image. In the embodiments of the present disclosure, the detection model can be assisted by the classification model and vice versa, in this way the functions of different AI models complement each other, the disadvantage of using one single model can be resolved, and the misinterpretation rate can be reduced.

In the embodiments of the present disclosure, the extensive results of interpretation generated by the classification model and the result based on pathological analysis are combined to obtain the relevance between the lesion and the anatomic landmark, and the best decision can be made through machine learning, hence overcoming the misinterpretation problems commonly seen in the prior art. For example, the current existing CNN classification model is inherently shift invariant and cannot accurately learn the information of relative positions between the lesion and the anatomic landmark, making it prone to incorrect interpretation when the lesion is small or under special circumstances (for example, the anatomic landmark detection model is unable to recognize the anatomic landmark completely covered by the lesion).

The present disclosure generates best prediction rules through machine learning, and the prediction rules can also be used in application fields other than the recognition of medical images.

The image analysis system and method of the present disclosure can learn the distribution of data-driven structure as well as the high-dimensional and abstract data structure, make objective interpretation without making subjective man-made rules, directly learn experts' experience and knowledge through training on data labeled by the experts and avoid the situation where the experts find it difficult giving clear-cut descriptions of their experience and knowledge. The disclosed image analysis system can be independently adapted to new data.

To summarize, the image analysis system and method of the present disclosure can increase the performance of the lesion screening system, have high interpretability, and the prediction rules can be applied to the fuzzy system and used as fuzzy rules.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A medical image analysis method, comprising:
reading an original medical image;
performing image classification and object detection on the original medical image to generate a first classification result and a plurality of object detection results by a plurality of complementary artificial intelligence (AI) models;
performing object feature integration and transformation on a first detection result and a second detection result among the object detection results to generate a transformation result by a features integration and transformation module; and
performing machine learning on the first classification result and the transformation result to generate an image interpretation result by a machine learning module and display the image interpretation result;
wherein the features integration and transformation module performs transformation on the first detection result and the second detection result to generate a scalar or a vector;
wherein when the features integration and transformation module performs transformation, based on the relation between plural quadrants and a lesion, according to a first positive correlation with a membership degree of angular, an area, a confidence or any combination thereof;
wherein when the features integration and transformation module performs transformation, based on the relation between an anatomic landmark and the lesion according to a second positive correlation with a reciprocal of a distance between the lesion and an anatomic landmark, the area of the lesion, the confidence of the lesion or any combination thereof.

2. The medical image analysis method according to claim 1, further comprising: when it is determined that a size of the original medical image is greater than a predetermined size threshold, adjusting the size of the original medical image to be smaller than the predetermined size threshold.

3. The medical image analysis method according to claim 1, wherein the complementary AI models comprise:
a first classification model used to analyze the original medical image to generate the first classification result for use as a disease classification result;
a lesion detection model used to analyze the original medical image to generate the first detection result, wherein the first detection result is a lesion detection result including information of a position, an area and a confidence of each lesion, and a total number of lesions for each lesion category; and an anatomic landmark detection model used to analyze the original medical image to generate the second detection result, wherein the second detection result is an anatomic landmark detection result including information of a position, a first length, a second length and a confidence of each anatomic landmark.

4. The medical image analysis method according to claim 3, wherein, the complementary AI models further comprise a second classification model receiving a target region cropped from the original medical image by the second detection model and analyzes the target region to generate a second classification result for being inputted to the machine learning module.

5. The medical image analysis method according to claim 1, wherein,
the first positive correlation between the quadrants and the lesion is relevant to a first operation result of the membership degree of angular and a first parameter, a second operation result of the area and a second parameter, and a third operation result of the confidence and a third parameter; and
the second positive correlation between the anatomic landmark and the lesion is relevant to a fourth operation result of the reciprocal of the distance between the lesion and the anatomic landmark and a fourth parameter, a fifth operation result of the area and a fifth parameter, and a sixth operation result of the confidence and a sixth parameter.

6. The medical image analysis method according to claim 5, wherein, the first parameter, the second parameter, the third parameter, the fourth parameter, the fifth parameter and the sixth parameter are obtained through data learning.

7. The medical image analysis method according to claim 6, wherein, the first parameter, the second parameter, the third parameter, the fourth parameter, the fifth parameter and the sixth parameter are updated through a backpropagation algorithm or Bayesian optimization.

8. The medical image analysis method according to claim 1, wherein,
the membership degree of angular is obtained using fuzzy logic, a plurality of fuzzy sets are defined;
when the membership degree of angular is represented by an angular membership function having an output value between 0 and 1; and
the angular membership function has a shape of a trapezoid, a triangle or any combination thereof, and the shape is trainable.

9. The medical image analysis method according to claim 1, wherein,
the first detection result is a lesion result matrix, and elements in each row of the lesion result matrix comprise: a category of the lesion, a position of the lesion, a horizontal length of the lesion, a vertical length of the lesion and a confidence of the lesion, and
the second detection result is an anatomic landmark result matrix, and elements in each row of the anatomic landmark result matrix comprise: a category of the anatomic landmark, a position of the anatomic landmark, a horizontal length of the anatomic landmark, a vertical length of the anatomic landmark and a confidence of the anatomic landmark.

10. The medical image analysis method according to claim 9, wherein,
the features integration and transformation module integrates and transforms the lesion result matrix and the anatomic landmark result matrix into a lesion and anatomic landmark relation matrix; and
the features integration and transformation module flattens the lesion and anatomic landmark relation matrix into a one-dimensional lesion and anatomic landmark relation vector, wherein the first classification result is a one-dimensional confidence vector.

11. The medical image analysis method according to claim 10, wherein, the machine learning module performs machine learning on the one-dimensional confidence vector and the one-dimensional lesion and anatomic landmark relation vector to generate the image interpretation result.

12. The medical image analysis method according to claim 11, wherein, the image interpretation result comprises a medical image having a lesion and an anatomic landmark and at least one interpretation result; and the original medical image comprises a fundus image or a non-fundus image.

13. A medical image analysis device, comprising
a processor; and
a display unit coupled to the processor,
wherein,
the processor is configured to:
read an original medical image;
perform image classification and object detection on the original medical image to generate a first classification result and a plurality of object detection results by a plurality of complementary artificial intelligence (AI) models;
perform object feature integration and transformation on a first detection result and a second detection result among the object detection results to generate a transformation result by a features integration and transformation module; and
perform machine learning on the first classification result and the transformation result to generate an image interpretation result by a machine learning module and display the image interpretation result on the display unit;
wherein the features integration and transformation module performs transformation on the first detection result and the second detection result to generate a scalar or a vector;
wherein when the features integration and transformation module performs transformation, based on the relation between plural quadrants and a lesion, according to a first positive correlation with a membership degree of angular, an area, a confidence or any combination thereof;
wherein when the features integration and transformation module performs transformation, based on the relation between an anatomic landmark and the lesion according to a second positive correlation with a reciprocal of a distance between the lesion and an anatomic landmark, the area of the lesion, the confidence of the lesion or any combination thereof.

14. The medical image analysis device according to claim 13, wherein, the processor is configured to: when it is determined that a size of the original medical image is greater than a predetermined size threshold, adjust the size of the original medical image to be smaller than the predetermined size threshold.

15. The medical image analysis device according to claim 13, wherein, the complementary AI models comprises:
- a first classification model used to analyze the original medical image to generate the first classification result for use as a disease classification result;
- a lesion detection model used to analyze the original medical image to generate the first detection result, wherein the first detection result is a lesion detection result including information of a position, an area and a confidence of each lesion, and a total number of lesions for each lesion category; and
- an anatomic landmark detection model used to analyze the original medical image to generate the second detection result, wherein the second detection result is an anatomic landmark detection result including information of a position, a first length, a second length and a confidence of each anatomic landmark.

16. The medical image analysis device according to claim 15, wherein, the complementary AI models further comprise a second classification model receiving a target region cropped from the original medical image by the second detection model and analyzes the target region to generate a second classification result for being inputted to the machine learning module.

17. The medical image analysis device according to claim 13, wherein,
- the first positive correlation between the quadrants and the lesion is relevant to a first operation result of the membership degree of angular and a first parameter, a second operation result of the area and a second parameter, and a third operation result of the confidence and a third parameter; and
- the second positive correlation between the anatomic landmark and the lesion is relevant to a fourth operation result of the reciprocal of the distance between the lesion and the anatomic landmark and a fourth parameter, a fifth operation result of the area and a fifth parameter, and a sixth operation result of the confidence and a sixth parameter.

18. The medical image analysis device according to claim 17, wherein, the first parameter, the second parameter, the third parameter, the fourth parameter, the fifth parameter and the sixth parameter are obtained through data learning.

19. The medical image analysis device according to claim 18, wherein, the first parameter, the second parameter, the third parameter, the fourth parameter, the fifth parameter and the sixth parameter are updated through a backpropagation algorithm or Bayesian optimization.

20. The medical image analysis device according to claim 13, wherein,
- the membership degree of angular is obtained using fuzzy logic, a plurality of fuzzy sets are defined;
- when the membership degree of angular is represented by an angular membership function having an output value between 0 and 1; and
- the angular membership function has a shape of a trapezoid, a triangle or any combination thereof, and the shape is trainable.

21. The medical image analysis device according to claim 13, wherein,
- the first detection result is a lesion result matrix, and elements in each row of the lesion result matrix comprise: a category of the lesion, a position of the lesion, a horizontal length of the lesion, a vertical length of the lesion and a confidence of the lesion, and
- the second detection result is an anatomic landmark result matrix, and elements in each row of the anatomic landmark result matrix comprise: a category of the anatomic landmark, a position of the anatomic landmark, a horizontal length of the anatomic landmark, a vertical length of the anatomic landmark and a confidence of the anatomic landmark.

22. The medical image analysis device according to claim 21, wherein,
- the features integration and transformation module integrates and transforms the lesion result matrix and the anatomic landmark result matrix into a lesion and anatomic landmark relation matrix; and
- the features integration and transformation module flattens the lesion and anatomic landmark relation matrix into a one-dimensional lesion and anatomic landmark relation vector, wherein the first classification result is a one-dimensional confidence vector.

23. The medical image analysis device according to claim 22, wherein, the machine learning module performs machine learning on the one-dimensional confidence vector and the one-dimensional lesion and anatomic landmark relation vector to generate the image interpretation result.

24. The medical image analysis device according to claim 23, wherein, the image interpretation result comprises a medical image having a lesion and an anatomic landmark and at least one interpretation result; and the original medical image comprises a fundus image or a non-fundus image.

25. The medical image analysis method according to claim 3, wherein the area of each lesion is calculated by a vertical length and a horizontal length of a bounding box detected by the lesion detection model.

26. The medical image analysis device according to claim 15, wherein the area of each lesion is calculated by a vertical length and a horizontal length of a bounding box detected by the lesion detection model.

* * * * *